(12) United States Patent
Hutmacher et al.

(10) Patent No.: US 11,830,377 B2
(45) Date of Patent: Nov. 28, 2023

(54) SURGICAL TRAINING DEVICE

(71) Applicant: QUEENSLAND UNIVERSITY OF TECHNOLOGY, Kelvin Grove (AU)

(72) Inventors: Dietmar Hutmacher, Kelvin Grove (AU); Nathan Castro, Kelvin Grove (AU); Onur Bas, Kelvin Grove (AU)

(73) Assignee: QUEENSLAND UNIVERSITY OF TECHNOLOGY, Kelvin Grove (AU)

( * ) Notice: Subject to any disclaimer, the term of this patent is extended or adjusted under 35 U.S.C. 154(b) by 735 days.

(21) Appl. No.: 16/765,239

(22) PCT Filed: Nov. 30, 2018

(86) PCT No.: PCT/AU2018/051286
§ 371 (c)(1),
(2) Date: May 19, 2020

(87) PCT Pub. No.: WO2019/104395
PCT Pub. Date: Jun. 6, 2019

(65) Prior Publication Data
US 2020/0294422 A1    Sep. 17, 2020

(30) Foreign Application Priority Data

Nov. 30, 2017  (AU) ............................... 2017904840

(51) Int. Cl.
*G09B 23/28*     (2006.01)
*A61B 17/04*     (2006.01)
*A61B 17/00*     (2006.01)

(52) U.S. Cl.
CPC .......... *G09B 23/28* (2013.01); *A61B 17/0401* (2013.01); *A61B 2017/00716* (2013.01)

(58) Field of Classification Search
CPC ......... G09B 23/28; G09B 23/30; G09B 23/32
See application file for complete search history.

(56) References Cited

U.S. PATENT DOCUMENTS 3,775,865 A * 12/1973 Rowan ................... G09B 23/28
                                                          434/262
4,386,917 A *  6/1983 Forrest .................. G09B 23/28
                                                          434/267

(Continued)

OTHER PUBLICATIONS

European Application No. 18883477.4, Extended European Search Report dated May 6, 2021, 6 pages.

(Continued)

*Primary Examiner* — Kurt Fernstrom
(74) *Attorney, Agent, or Firm* — Kilpatrick Townsend & Stockton LLP

(57) ABSTRACT

Disclosed is a suturing training device and a method of using the device. The device comprises a base having a first side and a second side, the base defining a plane. The device also comprises a first anchor and a second anchor positioned on the first side of the base. The first and second anchors are each connectable to a segment of tissue so that the tissue is suspended therebetween in use of the device. An actuator is associated with one or both of the first anchor and the second anchor. The actuator is actuatable to cause relative movement of the first and second anchors along the plane. A force gauge is configured to measure a force applied to the tissue when the first and second anchors are moved relative one another by the actuator.

30 Claims, 4 Drawing Sheets

(56) References Cited

U.S. PATENT DOCUMENTS

| | | | | |
|---|---|---|---|---|
| 5,149,270 A * | 9/1992 | McKeown | G09B 23/285 | 434/262 |
| 5,230,630 A * | 7/1993 | Burgett | G09B 23/28 | 434/262 |
| 5,358,408 A * | 10/1994 | Medina | G09B 23/28 | 434/262 |
| 5,873,732 A * | 2/1999 | Hasson | G09B 23/286 | 434/262 |
| 5,947,743 A * | 9/1999 | Hasson | G09B 23/286 | 434/262 |
| 6,398,557 B1 * | 6/2002 | Hoballah | G09B 23/28 | 434/262 |
| 8,403,676 B2 * | 3/2013 | Frassica | G09B 23/30 | 434/267 |
| 9,959,786 B2 * | 5/2018 | Breslin | G09B 23/285 | |
| 10,796,606 B2 * | 10/2020 | Felsinger | G09B 23/28 | |
| 2005/0032028 A1 * | 2/2005 | Chosack | G09B 23/32 | 434/262 |
| 2006/0252019 A1 | 11/2006 | Burkitt et al. | | |
| 2010/0009329 A1 | 1/2010 | Takanishi et al. | | |
| 2010/0256966 A1 * | 10/2010 | Cowley | G09B 23/30 | 703/11 |
| 2010/0273135 A1 * | 10/2010 | Cohen | G09B 23/28 | 434/267 |
| 2012/0171652 A1 * | 7/2012 | Sparks | G09B 23/28 | 434/262 |
| 2014/0057236 A1 * | 2/2014 | Meglan | G09B 23/30 | 434/274 |
| 2015/0371558 A1 | 12/2015 | Katayama et al. | | |
| 2018/0075777 A1 * | 3/2018 | Iverson | G09B 23/30 | |

OTHER PUBLICATIONS

International Application No. PCT/AU2018/051286, International Search Report and Written Opinion dated Mar. 6, 2019, 7 pages.

\* cited by examiner

SURGICAL TRAINING DEVICE

TECHNICAL FIELD

This disclosure relates generally to a device that is used as a training device to teach and evaluate suturing techniques of tissues such as small blood vessels, skin, tendon and ligament.

BACKGROUND

Suturing tissue is a skill doctors and surgeons develop through the use of training tools and devices. As their suturing skill improves, doctors and surgeons progress to more complex scenarios. Surgical suturing training devices typically employ silicone-based materials as a synthetic tissue analogue of real tissue. In some cases, the doctors and surgeons may use cadaveric and animal tissue for practical training on more natural tissue. Synthetic tissue analogues are useful for initial skill development and preoperative suture training, but they do not reflect the physiochemical properties of the natural tissue. Furthermore, the costs, accessibility, and preparation of cadaveric and animal tissue is time-consuming and impractical. In addition, cadaveric and natural tissue may only provide a proxy for living human tissue.

It is to be understood that, if any prior art publication is referred to herein, such reference does not constitute an admission that the publication forms a part of the common general knowledge in the art, in Australia or any other country.

SUMMARY

The disclosure provides a suturing training device comprising: a base having a first side and a second side; a first anchor and a second anchor positioned on the base, the first and second anchors are each connectable to a segment of tissue so that the tissue is suspended therebetween in use of the device; an actuator associated with one or both of the first anchor and the second anchor, the actuator being actuatable to cause relative movement between the first and second anchors; and a force gauge configured to measure a force applied to the tissue when the first and second anchors are moved relative one another by the actuator.

Providing a force gauge allows a user to obtain quantitative information about the quality of the suture inserted into the tissue. For example, the strength at which a suture breaks can be calculated. Visual inspection may also show a user how and why a suture failed and ways to improve their skills. Having an actuator move the first and second anchors relative to one another may also mean that a user can place the tissue under tension prior to suturing so that they may practice haptic suturing under conditions similar to that of tissue in its natural state i.e. in its in vivo state.

The term "tissue" is to be interpreted broadly to include materials of natural and synthetic origin, and combinations thereof manufactured to exhibit structural and physicochemical analogues with properties simulating tissues including skin, blood vessels, intestinal tissue and/or tendons or nerves.

In an embodiment, at least one of the anchors may comprise: a first anchor component having a recess; and a second anchor component that is receivable in the recess to be secured therein, the segment of tissue being connectable to the second anchor component. The first and second anchors may be configured to anchor tubular tissue. Tubular tissue may include soft tissues such as nerves, blood vessels, tendons and ligaments. The tubular tissue may be hollow, such as for blood vessels. The first and/or second anchor may be provided with a conduit that is sized so that the tubular tissue can be sleeved over an outside of the conduit so as to be coaxially arranged thereto. The anchor with the conduit may be configured so that the tubular tissue is in fluid communication with the conduit. This may allow a user to pump fluid into a hollow tubular tissue to assess the seal of the sutures. A pressure gauge may measure a pressure of a fluid pumped into the tubular tissue.

The force gauge may be associated with the first anchor. Alternatively, the force gauge may be associated with the second anchor. The force gauge may be associated with the actuator. The anchors may be positioned on the first side of the base. The first anchor may be supported on a first support and the second anchor may be supported on a second support. The force gauge may be located in one of the first or second supports, such as the first support. The first support may be in a fixed relationship relative to the base and the second support may be moveable relative to the first support. The second support may be slidably engaged with a track located on the base, such as laterally translatably engaged with the track. The actuator may connect the first anchor and second anchor.

The device may further comprise a camera mount that is moveable relative to the first and/or second sides so that a viewing angle of the camera is able to record use of the device from a plurality of angles. The camera mount may be moveable relative the second side. The camera mount may be configured to mount, including, for example, a smartphone so that a smartphone camera is used as the camera. The base may comprise an aperture that extends from the first side to the second side to provide a viewing window in the base to allow a user to view, in use of the device, the tissue from the second side.

The device may further comprise one or more legs connected to and extending away from the second side. The one or more legs may be adjustable to adjust a length between the base and a foot of the one or more legs. The actuator may further comprise a crank that is configured to be turned by a user of the device to move the first and second anchors relative one another. The crank may be manual or automatic and may be configured to respond to engagement with the user.

Also disclosed is a suturing training device comprising: two anchors that are moveable relative one another, each anchor is configured to anchor a segment of tissue thereat so the tissue is suspended between the two anchors; and wherein the device is configured so that movement of the anchors relative to one another applies a force to the tissue, the force being measured by a force gauge.

Having a device where the anchors are moveable relative to each other means that a preselected force may be applied to the tissue prior to suturing. Alternatively, once the suture has been inserted into the tissue, the anchors may be moved apart to test the mechanical properties of the suture. For example, if the tissue ruptures before the suture fails, this indicates that the suture is of sufficient quality. The device may be otherwise defined as set forth above.

Also disclosed is a suturing training system, comprising: a base having a first side and a second side, the base defining a plane; a first anchor and a second anchor positionable on the first side, the first and second anchors are each connectable to a segment of tissue so that, in use of the system, the tissue is suspended therebetween; an actuator connectable to one or both of the first and second anchors, the actuator being actuatable to cause relative movement of the first and second anchors along the plane; and a force gauge configured to measure a force applied to the tissue when the first and second anchors are moved relative one another by the actuator.

The system may comprise the device as set forth above.

Also disclosed is a suture training kit comprising: a first anchor and a second anchor, the first and second anchors are each connectable to a segment of tissue for suspending tissue therebetween; an actuator connectable to one or both of the first and second anchors, the actuator being actuatable to cause relative movement of the first and second anchors along the plane; and a force gauge connectable to one of the first or second anchors, the force gauge being configured to measure a force applied to the tissue in use of the device.

The kit may further comprise a base to which the first and second anchors are attachable to. The base may be manufactured by use of an additive manufacturing technique. The kit may comprise the device as set forth above. The kit may be contained in a package such as a box.

Also disclosed is a method of using a suturing training device comprising: providing a piece of tissue with a suture, connecting a first segment of the tissue to a first anchor and a second segment of the tissue to a second anchor so that the piece of tissue is suspended between the first and second anchors; moving the first and second anchors relative to one another to apply a force to the tissue; and measuring a force applied to the tissue.

Providing a tissue with a suture is to be interpreted broadly to include anchoring a piece of tissue with a suture already inserted into the first and second anchors, or anchoring a piece of tissue into the first and second anchors then inserting a suture into the tissue.

The step of providing the tissue with the suture may comprise inserting a suture into the tissue after the tissue has been suspended between the first and second anchors. The tissue may be provided as two pieces, where each piece of tissue has a segment that is connected to one of the first and second anchors. Providing a suture may comprise suturing the two pieces of tissue together to form a single piece of tissue. The step of providing the tissue with the suture may comprise inserting a suture into the tissue after the tissue has been suspended between the first and second anchors. The suture may be inserted into the tissue after the force is applied to the tissue. Alternatively, the suture may be inserted into the tissue before the force is applied. The method may further comprise moving the first and second anchors away from one another to test a strength of the suture. In this way, the method may be used to allow a user to insert sutures into tissue under tension and/or test the mechanical properties of the suture. The piece of tissue may be tubular tissue such as a blood vessel or similar analogue. The tissue may be provided as two pieces, where each piece of tissue has a segment that may be connected to one of the first and second anchors. Providing a suture may comprise suturing the two pieces of tissue together to form a single piece of tissue.

The method may comprise recording data including video footage and force measurements. The video footage may be recorded from a view point underneath the tissue so as to leave a user's view unobstructed during the method. The data may be remotely accessible. Recording data may allow a user to practice suturing tissue whilst being able to provide self-assessment. For example, medical education literature has shown the positive effects of self- and independent assessment on practical skill retention. Video capture and logging via a mobile application-based platform may allow for in-person self-assessment and may allow for remote external assessment of surgical technique for improved skill retention. The collection of data may also allow for real-time assessment by a third party remote from the user.

An often-overlooked component of practical surgical training is haptic response generated for soft tissues under tension. The device, system, kit and/or method, in combination with various synthetic and natural tissues and tissue analogues may allow for the placement of physiological loading mimicking, for instance, the tension of injured nerves, blood vessels, tendons, ligaments, etc. In addition to scenarios involving tissues/tissue analogues, the device, system, kit and/or method may aid in practical surgical training for the placement of natural and synthetic training grafts simulating structural and physicochemical properties of nerves, blood vessels, ligaments, tendons etc. in the presence or absence of mechanical stress. The force gauge can be laterally displaced to quantify the force necessary for failure of the suture inserted into the tissue by a user. When combined with data recording such as video capture via a smart phone application, qualitative and quantitative failure assessment may be realized, for example with an App on a smartphone.

BRIEF DESCRIPTION OF FIGURES

Embodiments will now be described by way of example only with reference to the accompanying non-limiting Figures.

DETAILED DESCRIPTION OF EMBODIMENTS

Figure 1:
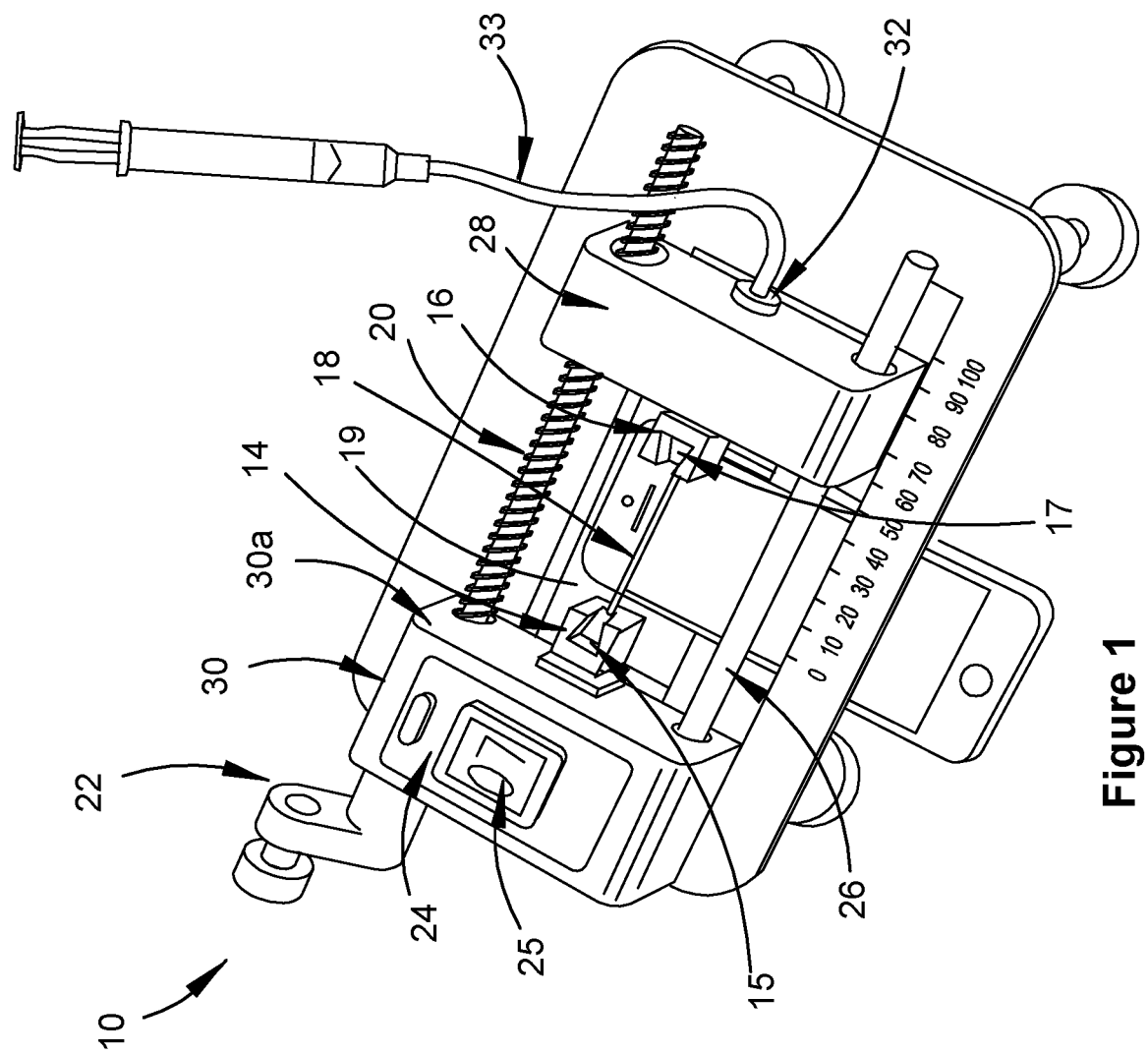
FIG. 1 shows a perspective view of a suturing training device.
Figure 2:
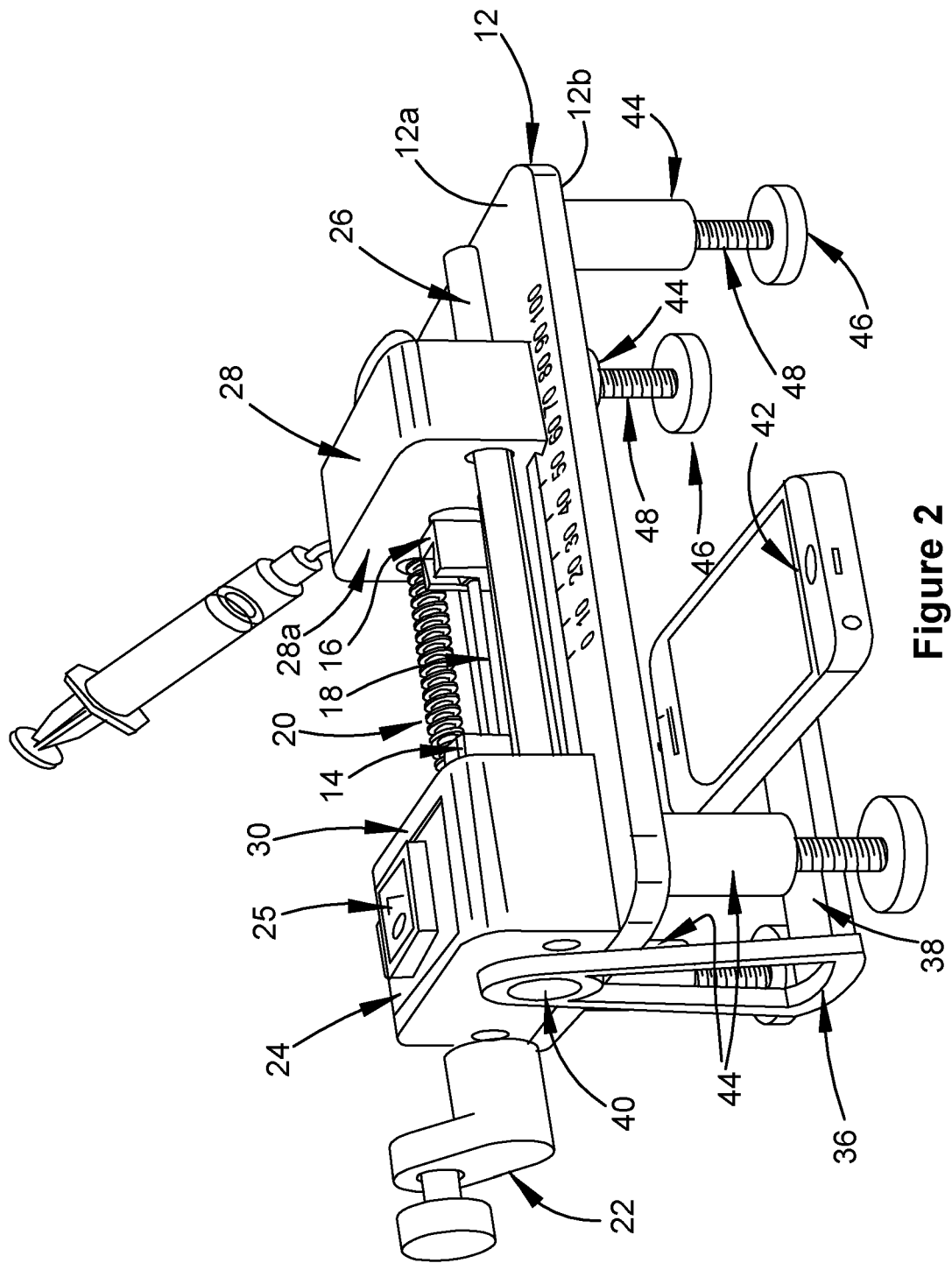
FIG. 2 shows another perspective view of FIG. 1
Figure 3:
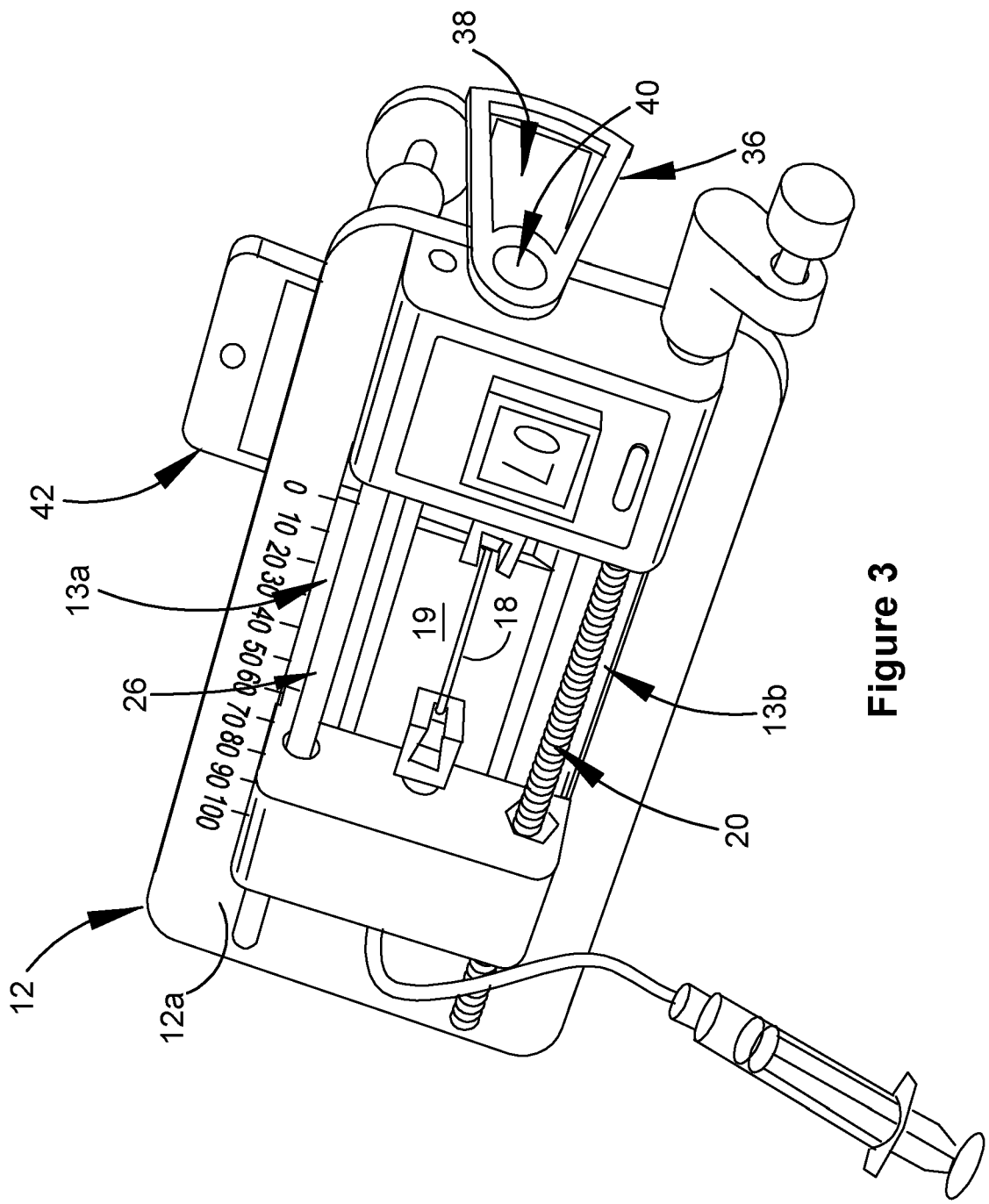
FIG. 3 shows another perspective view of FIG. 1.

FIGS. 1 to 3 show an embodiment of a suturing training device 10. The device 10 has a base in the form of plate 12. As shown in FIG. 2, the plate 12 has a first side shown as a top side 12a, and a second side, shown as a bottom side 12b. The terms top and bottom are relative and do not limit the device to any particular orientation. The plate 12 defines a plane. A first anchor in the form of first protrusion 14 having a recess 15 for receiving an anchoring component is associated with the top side 12a of the plate 12. The protrusion 14 is connected to a first support in the form of first end block 30 that is associated with the top side 12a of the plate 12. The device 10 also has a second anchor in the form of a second protrusion 16 having a recess 17 for receiving an anchoring component is associated with the top side 12a of the plate 12. The second protrusion 16 is connected to a second support in the form of second end block 28 that is associated with the top side 12a of the plate 12. In some embodiments the second end block 28 is provided as a plate. The first protrusion 14 and second protrusion 16 are connectable to tissue 18, via the anchoring components as is mentioned with reference to FIG. 4. In use of the device 10, the tissue 18 is suspended between the first protrusion 14 and second protrusion 16. Since the protrusions 14/16 are connected to the first and second end blocks, the combination of the protrusions and end blocks is generally referred to as an anchor.

An actuator is associated with one or both of the first and second anchors. In the embodiment of FIGS. 1 to 3, an actuator in the form of threaded rod 20 is associated with the first protrusion 14 and second protrusion 16. The threaded rod 20 engages with the first end block 30 and second end block 28. The second end block 28 has a threaded region such as a threaded bore that has a complementary thread to the threaded rod 20 so that the bore can engage with the threaded rod 20. The threaded bore can be provided by a nut. The threaded rod 20 passes through the first end block 30 so that it is retained therein, but in such a way that the threaded rod 20 can rotate around its longitudinal axis. This allows the threaded rod 20 near the second end block 28 to be screwed into or out of the threaded bore in the second end block 28. The threaded region can be mounted within the first end block 28 or to an outside surface thereof. In some embodiments a plate having an aperture with a threaded disposed on the inner surface of the aperture is used as the threaded region that is associated with the second end block 28. The embodiment shown in FIGS. 1 to 3 has the threaded bore being mounted within the first end block 28. In some embodiments the threaded rod 20 is secured to an outside surface of the first end block 30 and second end block 28. Attached at a terminus of the threaded rod 20 near the first end block 30 is a crank in the form of handle 22. In some embodiments the handle 22 is provided at the terminus of the threaded rod near the second end block 28. Rotation of the handle 22 around the longitudinal axis of the rod 20 causes the first end block 30 and second end block 28, thus the first and second protrusions 14/16, to move relative each other along the top surface 12a of the plate 12. Although the threaded rod 20 is depicted in the Figures as having a thread that extends along the entire length of the rod, in some embodiments the threaded section of the rod only extends along a portion of the rod 20.

In the embodiment of FIGS. 1 to 3, the first end block 30 is secured to the plate 12 in a fixed relationship so that it does not move. This means that rotation of the handle 22 results in movement of the second end block 28, and thus the second protrusion 16, along the longitudinal axis of the threaded rod 20 along the plane of the plate 12. However, in some embodiments both the first and second end blocks are in a slidable relationship with the plate 12. In these embodiments, the threaded rod 20 can have a right-handed thread for engagement with the second end block 28 and a left-hand thread for engagement with a complementary threaded bore, or vice versa, so that rotation of the rod 20 causes the first and second end blocks to move away or towards one another. In some embodiments, the actuator is only connected to the first end block 30 or the second end block 28, but in either case the first and second protrusions 14/16 are moveable relative one another. In some embodiments, the second end block 28 is fixed relative the plate 12 and the first end block 30 moves relative the plate 12 and second end block 30 to effect relative movement of the first and second protrusions 14/16.

The threaded rod 20 is manually actionable, but in some embodiments the handle may be replaced with a motor that can rotate the threaded rod 20 upon an input from a user or software input, such as a PCL input. Alternatively, the threaded rod 20 may be replaced with a linear actuator having a rod that can extend or retract.

The embodiment shown in FIGS. 1 to 3, the plate 12 has a track in the form of a first channel 13a and a second channel 13b. A surface of the second end block 28 that is in slidable contact with the top surface 12a of the plate 12 has a first flange and a second flange that extend into the first channel 13a and second channel 13b, respectively (not shown in Figures). Engagement of the flanges with the channels 13a/13b keeps the orientation of the second end block 28 generally perpendicular with respect to the threaded rod 20. This arrangement may help to ensure that the second end block 28 only moves back and forth in one direction relative to the first end block 30. The device 10 is also fitted with a support rod 26 that further limits any lateral and rotational movement of the second end block 28 so that its orientation is kept constant with respect to the threaded 20. Put another way, the track 13a/13b and support rod 26 may help to keep the mutually facing faces 28a and 30a of the first and second end blocks, respectively, parallel with one another during the relative movement of the first end block 30 and second end block 28. This helps to ensure that the first protrusion 16 and second protrusion 18 can only move with respect to one another in a single direction so that torsional and tangential forces are not transferred to the tissue 18. Although the first channel 13a and second channel 13b and support rod 26 are depicted in FIGS. 1 to 3, they are not required in all embodiments.

The first protrusion 16 is associated with a force gauge 24. In the embodiment of FIGS. 1 to 3, the force gauge 24 is directly connected to the first protrusion 16 and the force gauge 24 is also embedded in the first end block 30. In use of the device 10 when the tissue 18 is suspended between the first protrusion 14 and second protrusion 16, rotation of the handle 24 causes the threaded rod 20 to rotate which causes the second end block 28 to either move towards or away from the first end block 30 depending on the rotation direction of the handle. If the handle is rotated so that the second end block 28 moves away from the first end block 30, a tensile force is transferred to the tissue 18 provided that the distance between the first protrusion 14 and second protrusion 16 is greater than a length of the tissue in a relaxed form with no tension running through it. The tensile force transferred to the tissue is recorded by the force gauge 24. In some embodiments, the force gauge 24 is provided as a load cell. Because the distance between the first end block 30 and second end block 28 can be varied, and thus the distance between the first protrusion 14 and second protrusion 16, the amount of tension transferred from the device 10 into the tissue 18 can be adjusted by a user simply rotating the handle 22 to move the first protrusion 14 and second protrusion 16 relative once another to reach a desired tensile force.

A display 25 displays the force transferred to the tissue 18. In the embodiment of FIGS. 1 to 3, the number seven is displayed on the display 25 which indicates that 7N of force is being applied to the tissue 18. Because a force is exerted from the device 10 into the tissue 18, the device 10 is made of a material suitable to withstand these forces. Materials include metals, biological and/or synthetic plastic structures including structures prepared by additive manufacturing methods such as 3D printing. Because the device 10 is for training doctor's and surgeon's suturing techniques on tissues, the forces exerted onto the tissue 18 are relatively small, such as ranging from about 0.1N to about 200N. For example, the forces required to simulate suturing during micro surgery, such as blood vessels having a diameter of 2 mm, will generally be less than about 20N. For tendon repair, such as flexor tendon of the hand having a diameter of 2-3 mm, the force will generally be less than 50N. Therefore, the type(s) of tissue determine the forces that are required to be exerted onto the tissue 18. In some embodiments a force greater than 200N is exerted onto the tissue 18.

In other embodiments the force gauge is located in the second end block 28 (not shown). Since the purpose of the force gauge is to measure a tensile force that is transferred into the tissue 18, so long as the force gauge 24 is associated with the first protrusion 16 or second protrusion 18, this tensile force can be measured. Some embodiments have separate force gauges located in both the first end block 30 and second end block 28. The use of two force gauges can allow a user to measure any differences in forces applied along a longitudinal direction of the tissue 18 during suturing.

The device 10 also has legs in the form of pillars 44 attached to and extending away from the bottom side 12a of the plate 12, as best seen in FIG. 2. An end of the pillar 44 has a threaded bore which receives a threaded support 48 that terminates with a foot in the form of a pad 46. A distance from the bottom surface 12b to the plate 12 of the pad 46 is adjustable by screwing the threaded support 48 into or out of pillar 44. The pad 46 is designed to rest on a surface, such as a table. Having independently adjustable legs means that the orientation of the plate 12 with respect to a surface on which the device 10 is used can be adjusted. This can help to simulate different angles and conditions, which allows a user to train for different suturing scenarios for a given piece of tissue. In the embodiment of FIGS. 1 to 3 the pads 46 are rubberized so that they prevent accidental slippage of the device 10 in use by a user. In some embodiments the pads 46 are fixed relative the pillars 44.

In the embodiment of FIGS. 1 to 3 the device 10 is also fitted with a camera mount. In the embodiment of FIGS. 1 to 3, a bracket 36 is pivotably connected at one end to the first end block 30 at pivot point 40. The other end of the bracket 36 has a flange 38 extending away from the bracket 36. The flange 38 is sized to support a smartphone 42. In this way, the camera mounted to the camera mount is a smartphone camera. Because the flange 38 is pivotably connected to the first end block 30 through bracket 36, the camera is able to move relative to the plate 12 about an axis of rotation defined by pivot point 40. The pivot point may be passive so that it allows a user to simply pivot the flange 38 about pivot point 40, and in turn the camera from the smartphone 42, into any desired position. Alternatively, the pivot 40 may be active and include motors that are used to rotate the bracket 36 and flange 38 about pivot point 40. The flange 38 can have an anti-slip coating to prevent the smartphone 42 from slipping off when the bracket 36 and flange 38 are rotated about the pivot point 40.

The embodiments of FIGS. 1 to 3 show the camera mount hanging below the plate 12, i.e. the camera mount extends away from the second side 12b. This arrangement helps to keep a user's view free and unobstructed when they are using the device 10 e.g. inserting a suture into tissue 18. However, in some embodiments the camera mount can be positioned above the plate so as to be extending away from the first side 12a of the plate. In other embodiments, the camera mount is connected to an arm that is moveable relative to the first and second sides 12a/12b so that a viewing angle of the camera is able to view the tissue 18 from the top surface 12a and bottom surface 12b of the plate 12. Some embodiments may also have a camera mount that use a gimbal head to allow the camera to be rotated into a plurality of viewing angles. It should be noted that the camera mount is not required in all embodiments. For example, in some embodiments the camera mount is not used and the smartphone is placed onto a surface below the device 10.

The plate 12 has an aperture in the form of cut-away 19. Cut-away 19 acts as a viewing window in the plate 12 so that a user can view the tissue from the bottom side 12a in use of the device. For example, a user may pick up the device from a surface on which it was supported and inspect the sutures from the bottom side 12. In the embodiment of FIGS. 1 to 3, a width of the cut-away is delimited by edges of the tracks 13a and 13b. The cut-away 19 is not required in all embodiments. For example, the plate 12 can be made from a transparent material such as acrylic plastic to allow a user and/or camera to view the tissue and any associated suture from the bottom side 12b of the plate 12.

Figure 4:
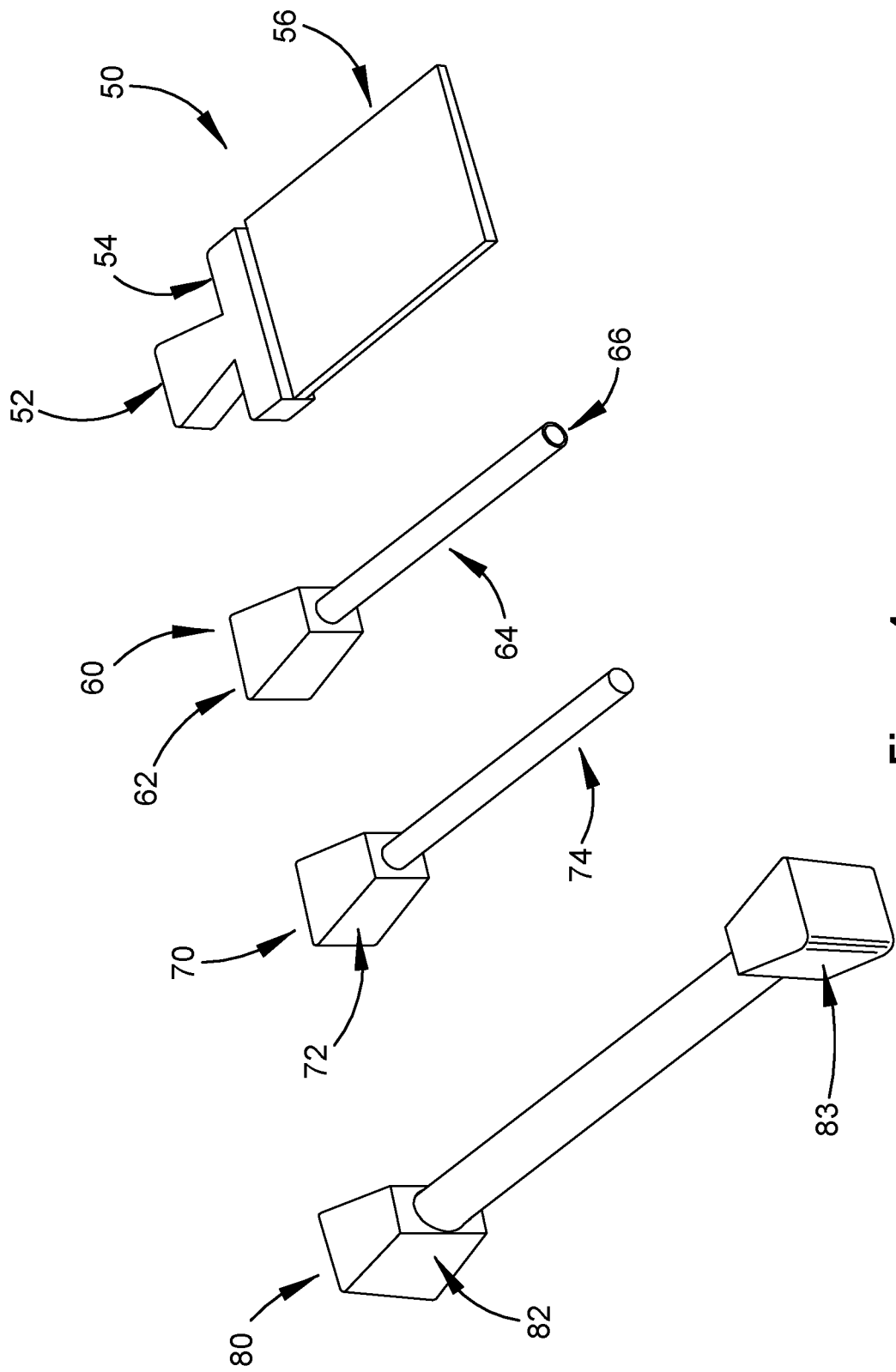
FIG. 4 shows an embodiment of tissue types and associated clamping means used in the suturing device.

Embodiments of anchoring components are shown in FIG. 4. In an embodiment, anchoring component 50 has a wedge-shaped head 52 that is connected to a laterally extending bar 54. A channel in the bar 54 can receive generally planar tissue 56, such as skin. A clamping means, such as a clamp, secures the planar tissue to the bar 54 (not shown). The clamp may also be actuated upon placement of the planar tissue 56 into the anchoring component 50. In some embodiments the bar is provided in two parts and the tissue is received therebetween so as to be clamped between the two parts. In some embodiments the planar tissue is secured to bar 54 using an adhesive. Adhesives may be used in addition to the clamping means. The protrusions 14/16 have a recess that is able to accommodate the wedge-shape head so that the anchoring component 50 is secured to the protrusion 14/16 in use of the device 10, but that can also be removed when a user wishes to change the tissue and/or tissue type. In another embodiment, anchoring component 60 connects to hollow tubular tissue 64, such as blood vessels, having an inner passage 66. Similar to anchoring component 50, anchoring component 60 has a wedge-shaped head that fits into a similarly sized recess (e.g. 15 or 17) in the first and second protrusions. Anchoring component 60 has a conduit (not shown) that is in fluid communication with the passage 66. To connect the tubular tissue 64 to the anchoring component 60, the tissue 64 is sleeved over an outside of the conduit so as to be coaxially arranged thereto i.e. the conduit is inserted into passage 66. A clamping means, such as a clamp, an O-ring, wire, etc., is then applied around the tissue 64 sleeved over the conduit to secured the tubular tissue 64 to the anchoring component 60. Anchoring component 70 is similar to anchoring component 60, except that anchoring component 70 is not provided with a conduit. Instead, wedge-shaped head 72 has a bore (not shown) into which rod-shaped tissue, such as tendon, can be inserted into. A clamping means applies a compressive force onto tissue 74 to secured the tissue 74 to the wedge-shaped head 72. The anchoring component 80 is similar to anchoring component 70 except that the bore (not shown) and wedge-shaped head 82 are larger to accommodate tissue with a larger diameter. In some embodiments an adhesive is used to secure and affix tissue to the wedge-shaped head. In some embodiments, the anchoring components allow the tissue to rotate around a longitudinal axis extending between the first and second protrusions 14/16. In some embodiments each of the wedge-shaped heads 52, 62, 72 and 82 have the same dimensions.

Although a wedge-shaped head is depicted for anchoring component 50/60/70/80, the disclosure is not limited to the geometries of these heads, and other ways of anchoring the head of the anchoring component to the respective protrusion can be used. For example, a head shape and protrusion that allow for an interference fit that can resist the forces applied to the anchoring component in use, a grub screw engaging on a member, a bayonet fitting, screw engagement and the like can be used to secure the anchoring component to the protrusions. Whatever form the anchoring component takes, the protrusion will have a complementary shape or fitting for secure engagement. In one embodiment the head of the anchoring component has a generally square shape and a generally elongate neck extends therefrom, and the tissue is fixable to the neck directly or indirectly. The recess into which the head is receivable in the protrusion 14 or 16 is fitting with a slotted opening that accommodated the neck but that rests against a portion of the head so that the head is securely received in the recess.

For clarity only, one anchoring component 50/60/70 is shown attached to tissue 56/64/74 respectively, but in use of the device 10 the shown free end of the tissue 56/64/76 would also have an anchoring component attached thereto, similar to anchoring component 80 having a wedge-shaped head 82 for engagement with the recess 15 of the first protrusion 14 and a second wedge-shaped head 83 for engagement with the recess 17 of the second protrusion 16 so that it can be suspended between the first and second protrusions as shown in FIGS. 1 to 3. Further, it can be advantageous for each of the wedge-shaped heads to have the same dimensions and geometries so that a use can easily swap between tissue types. For example, a user may first practice suturing on a skin-analogue then switch over to a blood-vessel-analogue. The anchoring components in FIG. 4 are exemplary only and may be dimensioned so that they can be used to secure a variety of tissue(s) to the device. The types of tissue that can be secured to the device 10 through the anchoring components include natural and/or synthetic analogues of planar tissue such as skin, tubular tissue such as blood vessels, and elongate tissue such as nerves, tendon and ligaments.

For the embodiments where tubular tissue is secured to the device, the device can further comprise a conduit 32 in the second end block 28. Conduit 32 will generally be sized to accommodate a luer lock fitting. Conduit 32 is in fluid communication with the second protrusion 16 and the anchoring component 60 to allow a fluid to be passed into tubular tissue e.g. 64. Seals such as O-rings can be used to prevent fluid from leaking from the second protrusion 16 and the associated anchoring component 60. For example, when a user is practicing suturing blood vessels, the user may pump a fluid into the blood vessel through conduit 32 to assess whether or not the suture is adequate to prevent unwanted fluid leakage from the region of tissue that has been sutured. In some embodiments, a pressure gauge is in fluid communication to allow a pressure of the fluid pumped into the hollow tissue to be measured (not shown). This can be used to simulate the in vivo conditions for tissue such as blood vessels. A pump is used in some embodiments to pump fluid into the tissue. A pulsed or steady state fluid flow can be used. The pump may be a syringe. In the embodiment of FIGS. 1 to 3 a flexible tube 33 connects a syringe 34 to conduit. However, in some embodiments, the syringe is connected directly to conduit 32. A conduit is also located in first end block 30 in place of or in addition to the conduit 32. In some embodiments both the first and second end blocks 30/28 have a conduit to allow flow of fluid through tubular tissue.

In some embodiments, the device is provided as individual components that a user can assemble. In this way, the suturing training device is provided as a system. In another embodiment, the disclosure provides a suture training kit. The kit comprises the first protrusion and second protrusion 16, the threaded rod 20 and the force gauge 24 and optionally support rod 26. In some embodiments, the first and second protrusions 14/16 are already secured to the first and second end bodies 30/28 respectively, but in other embodiments a user may assemble them during assembly of the device. The kit optionally is provided with the plate 12. However, in some embodiments a user manufactures the base using an additive manufacturing technique such as 3D printing. For example, the kit can comprise a web link that a user can access to download a file that is executable on an additive manufacturing device to print the plate 12.

To use the device 10, anchoring components are connected at or near ends of a piece of tissue. One of the anchoring components is secured to the first protrusion 14 and the other of the anchoring components is secured to the second protrusion 16. This results in the piece of tissue being suspended between the first 14 and second 16 protrusion. The tissue is generally connected to the first and second protrusions 14/16 in an un-tensioned state. The handle 22 is turned so that the second end block 28 is caused to move away from the first end block 30. This movement causes the distance between the first protrusion 14 and second protrusion 16 to increase. Once this distance approaches and/or extends past a length of the tissue in an un-tensile state, a tensile force is applied to the tissue. Because the first protrusion 14 is associated with the force gauge 24, a force applied to the tissue can then be measured.

Once a force has been applied to the tissue, a suture can then be inserted into the tissue by a user. In these embodiments, the user can practice suturing with a haptic response to tissue under tension. Tissue under tension i.e. haptic suturing conditions tends to more accurately simulate natural tissue in vivo. The force applied to the tissue will be preselected depending on the tissue type. For example, the simulated tension requirements for blood vessels will differ to those required for tendon. Because the force is adjustable by moving the send end block 28 relative to the first end block 30 by rotating the handle 24 in the desired direction, and because the anchoring component can easily be swapped to accommodate different tissue types, a user can use the device to quickly change between tissue types and suturing conditions. In some embodiments an actuator is used to provide a fluctuating force to the tissue.

Once the suture has been inserted, the second end block 28 is moved away from the first end block 30 to increase the distance between the first and second protrusions 14/16. This increases the force applied to the tissue. Once the force is above a threshold amount, either the suture will fail, or the tissue will fail. The point and type of failure can provide the user with a qualitative assessment of their suturing ability. However, the force gauge provides a force reading when the suture or tissue breaks, thereby providing a quantitative assessment to the user. The data generated by the force gauge can be downloaded to a datalogger, computer or program, such as an Application on a smartphone for further analysis. If the tissue breaks before the suture, this generally indicates that the suture is of suitable quality, but the force of breakage would need to be assessed against a standard for a tissue. For example, if the tissue has a normal breaking force of 50N but the tissue surrounding the suture breaks at 40N, then this indicates that the locations of the sutures may not be suitable e.g. they may have been placed too close to an edge of the tissue. Since the device 10 can be used to test the strength of a suture, in some embodiments the tissue is already provided with a suture and the strength of the suture in the tissue is tested.

In embodiments where a camera mount is provided to mount a smartphone 42, the suturing procedure is recorded by the camera by viewing through the cutaway 19. The video data is used to provide qualitative assessment of the suturing procedure by either self-assessment from the user or from a third party such as a trained surgeon. Since the camera mount extends away from the bottom side 12b of the plate 12, the video records footage of the suturing procedure from below the plate 12. Having the camera mount below the plate 12 means that a user's vision is not obstructed by the camera mount e.g. flange 38 etc. so that they may concentrate on suturing. It also means that the back side of the tissue, that is the side of tissue facing away from the user, is able to be recorded so that a user can see how the back side of the tissue and sutures behaves during suturing. This allows a user to gain further qualitative assessment on their suturing skills. However, in some embodiments, the camera mount is on the top side 12a of the plate. Obstructing the user's view of the tissue may also provide more realistic simulations of suturing tissue in difficult to reach locations in vivo.

When data associated with the force gauge is also included with the video data, a qualitative and quantitative assessment can be made. The data generated during use of the device 10 in some embodiments is remotely assessable. For example, a supervisor can access the data to provide feedback to a user of the device. This allows remote supervision of a user's suturing skill progression. In some embodiments the force gauge 24 communicates with an Application of the smartphone wirelessly. Synchronous capture of video data and force gauge data can help to corroborate the failure mode. Having the data remotely accessible can alleviate the requirement for local data storage and archiving. It may also allow comparative analysis with other users, such as between groups of students.

In the embodiments of FIGS. 1 to 3, the piece of tissue is a tubular tissue that is an analogue of tissue such as blood vessels. In some embodiments the tissue is a blood vessel analogue having a diameter ranging from about 1 mm to 5 mm. Such fine tissue analogues can allow an experienced surgeon to practice and fine tune their skills for specific surgeries since the tissue analogue can be constructed as a life-sized replica of a patient. This also extends to other tissue types such as skin, tendon, nerve and ligament.

Video capture and logging via a mobile application-based platform of use of the device 10 by a user allows, in some embodiments, for in-person self-assessment and for remote external assessment of surgical technique for improved skill retention. The collection of data also allows for real-time assessment by a third part remote from the user in some embodiments.

EXAMPLES

Embodiments will now be described with reference to the accompanying non-limiting example.

Different tissue types were tested to failure using an embodiment of the device 10, as outlined in Table 1.

The tissue analogues used in these tests are tubular or planar composite materials consist of sheet-like 3D printed microfibers and an elastomeric matrix. Planar Tissue Analogue Type 1 and Flat Tissue Analogue Type 1 consist of silicone elastomeric matrix and 3D printed fibres. The overall dimensions of the Flat Tissue Analogue Type 1 and 2 are 50 mm×50 mm with a thickness of 1 mm.

Tubular Tissue Analogue Type 1 and Tubular Tissue Analogue Type 1 consist of silicone elastomeric matrix and 3D printed fibres. The overall dimensions of the Flat Tissue Analogue Type 1 are 30 mm in length, 2 mm in diameter and 500 μm in wall thickness. The overall dimensions of the Flat Tissue Analogue Type 2 are 30 mm in length, 4 mm in diameter and 500 μm in wall thickness.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the device, system, kit, and method.

The invention claimed is:

1. A suturing training device comprising:
a base having a first side and a second side;
a first anchor and a second anchor each positionable on the base, the first and second anchors are each connectable to a segment of tissue so that the tissue is suspended therebetween in use of the device;
an actuator associated with one or both of the first anchor and the second anchor, the actuator being actuatable to cause relative movement of the first and second anchors; and
a force gauge configured to measure a force applied to the tissue when one or both of the first and second anchors are moved relative one another by the actuator.

2. A device according to claim 1, wherein the first and second anchors are configured to anchor tubular tissue or planar tissue.

3. A device according to claim 2, wherein the first and/or second anchor is provided with a conduit that is sized so that the tubular tissue can be sleeved over an outside of the conduit so as to be coaxially arranged thereto, the anchor with the conduit being configured so that the tubular tissue is in fluid communication with the conduit.

4. A device according to claim 1, wherein the force gauge is associated with the first anchor.

5. A device according to claim 1, wherein the first anchor is supported on a first support and the second anchor is supported on a second support.

TABLE 1

The results of the tests performed to measure the strength of the sutures using the force gauge of the microsurgery training device.

| | Suture Failure Maximum Force (N) | | | |
|---|---|---|---|---|
| | Planar Tissue Analogue Type 1 | Planar Tissue Analogue Type 2 | Tubular Tissue Analogue Type 1 | Tubular Tissue Analogue Type 2 |
| Participant 1 | 2.44 | 1.23 | 0.42 | 0.67 |
| Participant 2 | 2.16 | 0.97 | 0.24 | 0.63 |
| Participant 3 | 3.57 | 0.92 | 0.29 | 0.45 |

6. A device according to claim 5 wherein the force gauge is located in the first support.

7. A device according to claim 5, wherein the first support is in a fixed relationship relative to the base and the second support is moveable relative to the first support, the second support being slidably engaged with a track located on the base.

8. A device according to claim 1, further comprising a camera mount that is moveable relative to the first and/or second sides so that a viewing angle of the camera is able to record use of the device from a plurality of angles.

9. A device according to claim 8, wherein the camera mount is moveable relative the second side.

10. A device according to claim 8, wherein the camera mount is configured to mount a smartphone having a camera wherein the smartphone camera is capable of use as the camera.

11. A device according to claim 1, wherein the base comprises an aperture that extends from the first side to the second side to provide a viewing window in the base to allow a user to view, in use of the device, the tissue from the second side.

12. A device according to claim 1, further comprising one or more legs connected to and extending away from the second side.

13. A device according to claim 12, wherein the one or more legs are adjustable to adjust a distance between the base and a foot of the one or more legs.

14. A device according to claim 1, wherein the actuator further comprises a crank that is configured to be turned by a user of the device to move the first and second anchors relative one another.

15. A device according to claim 1, wherein at least one of the anchors comprises:
 a first anchor component having a recess; and
 a second anchor component that is receivable in the recess to be secured therein, the segment of tissue being connectable to the second anchor component.

16. A device according to claim 1, wherein the anchors are positioned on the first side of the base.

17. A suture training kit comprising:
 a first anchor and a second anchor, the first and second anchors are each connectable to a segment of tissue for suspending tissue therebetween;
 an actuator connectable to one or both of the first and second anchors, the actuator being actuatable to cause relative movement of the first and second anchors along a plane; and
 a force gauge configured to measure a force applied to the tissue when the first and second anchors are moved relative one another by the actuator.

18. A kit according to claim 17, further comprising a base to which the first and second anchors are attachable to.

19. A kit according to claim 18, wherein the base is manufactured by use of an additive manufacturing technique.

20. A method of using a suturing training device comprising:
 providing a piece of tissue with a suture,
 connecting a first segment of the tissue to a first anchor and a second segment of the tissue to a second anchor so that the piece of tissue is suspended between the first and second anchors;
 moving one or both of the first and second anchors relative to one another to apply a force to the tissue; and
 measuring a force applied to the tissue by a relative movement between the first and second anchors.

21. A method according to claim 20, wherein the step of providing the tissue with the suture comprises inserting a suture into the tissue after the tissue has been suspended between the first and second anchors.

22. A method according to claim 21, wherein the tissue is provided as two pieces, where a first piece of tissue has a segment that is connected to one of the first and second anchors and the second piece of tissue is connected to the other of the first and second anchors, and wherein providing the suture comprises suturing the two pieces of tissue together to form a single piece of tissue.

23. A method according to claim 21, wherein the suture is inserted into the tissue after the force is applied to the tissue.

24. A method according to claim 20, further comprising moving the first and second anchors away from one another to test a strength of the suture.

25. A method according to claim 20, further comprising recording data including video footage and force measurements.

26. A method according to 25, wherein the video footage is recorded from a view point underneath the tissue so as to leave a user's view unobstructed during the method.

27. A method according to claim 25 wherein the data is remotely accessible.

28. A method according to claim 20, wherein the piece of tissue is tubular tissue or planar tissue.

29. A suturing training device comprising:
 two anchors that are moveable relative one another, each anchor is configured to anchor a segment of tissue thereat so the tissue is suspended between the two anchors; and
 wherein the device is configured so that a relative movement between the anchors relative to one another applies a force to the tissue, the force being measured by a force gauge.

30. A suturing training system, comprising:
 a base having a first side and a second side, the base defining a plane;
 a first anchor and a second anchor positionable on the base, the first and second anchors are each connectable to a segment of tissue so that, in use of the system, the tissue is suspended therebetween;
 an actuator connectable to one or both of the first and second anchors, the actuator being actuatable to cause relative movement of the first and second anchors along the plane; and
 a force gauge configured to measure a force applied to the tissue when one or both of the first and second anchors are moved relative one another by the actuator.

* * * * *